(12) United States Patent
Paris et al.

(10) Patent No.: US 10,906,849 B2
(45) Date of Patent: Feb. 2, 2021

(54) EXPLOSIVE COMPOSITION AND METHOD OF DELIVERY

(71) Applicant: Dyno Nobel Asia Pacific Pty Ltd, Southbank (AU)

(72) Inventors: Nathan Paris, Mount Thorley (AU); Jeff Gore, Mount Thorley (AU); Paul Thornley, Mount Thorley (AU)

(73) Assignee: Dyno Nobel Asia Pacific Pty Limited, Southbank (AU)

( * ) Notice: Subject to any disclaimer, the term of this patent is extended or adjusted under 35 U.S.C. 154(b) by 391 days.

(21) Appl. No.: 15/521,959

(22) PCT Filed: Oct. 27, 2015

(86) PCT No.: PCT/AU2015/050666
§ 371 (c)(1),
(2) Date: Apr. 26, 2017

(87) PCT Pub. No.: WO2016/065412
PCT Pub. Date: May 6, 2016

(65) Prior Publication Data
US 2018/0009723 A1 Jan. 11, 2018

(30) Foreign Application Priority Data

Oct. 27, 2014 (AU) ................................ 2014904283

(51) Int. Cl.
| | | |
|---|---|---|
| *C06B 31/06* | (2006.01) | |
| *C06B 23/00* | (2006.01) | |
| *C06B 47/14* | (2006.01) | |
| *C01B 21/38* | (2006.01) | |
| *C07C 53/08* | (2006.01) | |

(52) U.S. Cl.
CPC ............ *C06B 31/06* (2013.01); *C06B 23/001* (2013.01); *C06B 23/004* (2013.01); *C06B 47/14* (2013.01); *C06B 47/145* (2013.01); *C01B 21/38* (2013.01); *C07C 53/08* (2013.01)

(58) Field of Classification Search
CPC ................................ C06B 31/06; C06B 23/00
See application file for complete search history.

(56) References Cited

U.S. PATENT DOCUMENTS

| | | |
|---|---|---|
| 3,210,160 A | 10/1965 | Gordon |
| 3,247,033 A | 4/1966 | Gordon |
| 3,294,601 A | 12/1966 | Gordon |
| 3,347,722 A | 10/1967 | Gordon |
| 3,854,400 A | 12/1974 | Van Langenhoven |
| 4,104,092 A | 8/1978 | Mullay |
| 4,439,254 A | 3/1984 | Mullay |
| 4,500,369 A | 2/1985 | Tag et al. |
| 4,836,870 A | 6/1989 | Cunningham et al. |
| 4,842,790 A * | 6/1989 | Nunnelly .................. B01J 2/12 118/303 |
| 4,872,929 A | 10/1989 | Mullay |
| 4,995,925 A | 2/1991 | Engsbraten |
| 5,159,153 A | 10/1992 | Cranney et al. |
| 5,271,779 A | 12/1993 | Engsbraten |
| 5,567,911 A | 10/1996 | Ekman |
| 5,608,185 A * | 3/1997 | Granholm ............... C06B 23/02 102/332 |
| 6,955,731 B2 | 10/2005 | Waldock |
| 7,938,920 B2 | 5/2011 | Waldock |
| 8,568,543 B2 | 10/2013 | Waldock |
| 2004/0144456 A1 | 7/2004 | Waldock |
| 2011/0209804 A1 | 9/2011 | Waldock |
| 2012/0282680 A1 * | 11/2012 | Goodridge ......... C12N 15/8259 435/262.5 |
| 2014/0090757 A1 * | 4/2014 | Pienaar ................. C06B 23/004 149/46 |

FOREIGN PATENT DOCUMENTS

| | | |
|---|---|---|
| CA | 1328351 | 4/1994 |
| CA | 2113945 | 8/1994 |
| CN | 1368944 | 9/2002 |
| WO | 199921809 | 5/1999 |
| WO | 2000078694 | 12/2000 |
| WO | 2000078694 A1 | 12/2000 |
| WO | 2004067478 | 8/2004 |
| WO | 2013131139 A1 | 9/2013 |

OTHER PUBLICATIONS

Erode,G. M. et al., Ammonium Nitrate Explosives for Civil Applications, Slurries, Emulsions and Ammonium Nitrate Fuel Oils ,2013.
ISO; PCT Written Opinion for copending International Application No. PCT/AU2015/050666, dated, Jan. 18, 2016 (4 pages).
ISO; PCT International Search Report for copending International Application No. PCT/AU2015/050666, dated, Jan. 18, 2016 (4 pages).

\* cited by examiner

*Primary Examiner* — Aileen B Felton
(74) *Attorney, Agent, or Firm* — Stoel Rives LLP

(57) ABSTRACT

Disclosed herein is an explosive composition for soft and wet ground. The explosive composition comprises an explosive comprising an oxidiser component in a water in oil emulsion or a water gel, and a bulking agent comprising discrete particles of a combustible substance. The combustible substance is water soluble but, in the explosive composition, migration of the combustible substance from the discrete particles to the oxidiser component is inhibited. Also disclosed is a method for delivering an explosive composition to a borehole, for example a borehole in soft and wet ground.

34 Claims, No Drawings

EXPLOSIVE COMPOSITION AND METHOD OF DELIVERY

CROSS-REFERENCE TO RELATED APPLICATIONS

This application is a national stage entry of International PCT Application No. PCT/AU2015/050666, which was filed 27 Oct. 2015, and claims priority to Australian Patent Application No. AU2014904283, which was filed on 27 Oct. 2014. The entire disclosures of these PCT and Australian patent applications are incorporated herein by reference.

TECHNICAL FIELD

The present invention relates to explosive compositions. In particular, the present invention relates to explosive compositions suitable for use in soft and wet ground, and to methods for delivering such explosive compositions into boreholes.

BACKGROUND ART

In certain situations, and especially when the ground to be blasted is soft and wet, explosive compositions having specific properties are required. The explosive compositions must firstly not be adversely affected by water and, secondly, must have a relatively low explosive strength. Explosive compositions in the form of emulsions and water gels often have good water resistance and may therefore be suitable for use in wet boreholes, but such explosive compositions are typically too powerful for use in soft ground.

Explosive compositions in which bulking agents are used to reduce the energy of an explosion are known. Bulking agents comprising, for example, microballoons, perlite, expanded polystyrene beads, vegetable matter such as legumes, rice hulls and organic fibres, saw dust, wood flour and wood pulp have been used to reduce the explosive energy (per volume) of explosive compositions. However, such bulking agents can often destabilise emulsions, whereby crystallisation of components in the emulsion can occur, leading to undesirable and detrimental changes to the explosive properties of the explosive composition. Such bulking agents can also have a high degree of variability in their physical (e.g. density, size distribution, etc.) and chemical (e.g. composition, compatibility, etc.) characteristics, which can lead to storage, handling or processing difficulties, as well as potentially inconsistent explosive properties.

WO 2013/131139 discloses explosive compositions comprising an aqueous emulsion of an oxidiser component, a hydrocarbon fuel component containing emulsifier, and a bulking agent being a fuel-type waste material in a solid particulate form substantially lacking rough surfaces and sharp edges. Providing the bulking agent in a solid particulate form substantially lacking rough surfaces and sharp edges was found to not promote crystallisation of the emulsion. However, sourcing and processing appropriate waste material into such a form can take a significant amount of time and effort, and may not be feasible or cost-effective.

It would be advantageous to provide alternative explosive compositions for use in soft and wet ground.

SUMMARY OF INVENTION

In a first aspect, the present invention provides an explosive composition for soft and wet ground. The explosive composition comprises an explosive comprising an oxidiser component in a water in oil emulsion or a water gel, and a bulking agent comprising discrete particles of a combustible substance. The combustible substance is water soluble but, in the explosive composition, migration of the combustible substance from the discrete particles to the oxidiser component is inhibited.

At the time of making the invention disclosed in WO 2013/131139, it was expected that bulking agents would need to be formed from materials that would not be able to physically or chemically interact with the emulsion disclosed therein, otherwise the bulking agent could destabilise the emulsion (and vice versa), potentially affecting the explosive properties of the composition. Thus, providing the bulking agent in a solid particulate form substantially lacking rough surfaces and sharp edges did not provide a means for disruption, and therefore crystallisation, of the emulsion droplets. Further, bulking agents made from waste materials such as plastics are substantially chemically inert with respect to the emulsion (especially the aqueous phase, which is where the oxidiser is contained), but, as noted above, sourcing and processing such waste material into a form whereby it does not destabilise the explosive emulsion can be problematic.

The inventors have surprisingly discovered that substances which had been expected to chemically interact with and potentially destabilise explosive compositions (e.g. by causing crystallisation of the oxidiser in the emulsion or water gel component of the composition) can, in fact, be used as bulking agents. In particular, the inventors discovered that bulking agents comprising water soluble (and combustible) substances that could potentially chemically interact with an emulsion or water gel upon contact can, in fact, be used in explosive compositions, provided that migration of the substance from the bulking agent to the oxidiser component is inhibited.

The inventors discovered that providing water soluble (and combustible) substances in the form of discrete particles inhibits migration of the substance from the discrete particles to the oxidiser component, at least for the time periods during which the explosive and the bulking agent would spend in mixed form in practice before detonation. Furthermore, as described below, additional factors may further inhibit migration of the substance from the discrete particles to the oxidiser component in the explosive composition. As such, bulking agents in accordance with the present invention do not tend to destabilise the explosive composition, despite the bulking agents and explosive being intimately admixed.

In some embodiments, the combustible substance has a negative oxygen balance. As described herein, using bulking agents having a negative oxygen balance may provide significant additional advantages, such as post-blast fume mitigation.

In some embodiments, the combustible substance is an agricultural substance such as a fertiliser. Fertilisers are usually readily available, relatively cheap, and are often provided in prilled or granulated forms, making them suitable for use in the present invention without necessarily requiring any further processing. The combustible substance may, for example, be selected from the group consisting of urea, ammonium sulphate, diammonium phosphate (DAP), calcium ammonium nitrate, monoammonium phosphate (MAP), zinc sulphate, ammonium sulphate nitrate and mixtures thereof.

In some embodiments, the bulking agent is provided in the form of discrete particles having smooth outer surfaces. Such particles are even less likely to have rough surfaces and sharp edges which might promote crystallisation or otherwise destabilise the explosive composition. Such particles may also be more resistant to being dissolved by components of the emulsion or water gel, which can help to further inhibit migration of the combustible substance. Furthermore, providing the bulking agent in the form of discrete particles having smooth outer surfaces may help to improve the processability of the bulking agent (and explosive composition), for example, by making it easier to pour or otherwise transfer.

In some embodiments, the bulking agent is provided in the form of prills or granules. Prills and granules are two kinds of particles which are readily formable using conventional processing equipment, and which typically have smooth outer surfaces and a relatively consistent particle size. Further, as prilled and granular materials are commonly used in the explosives industry, such prilled and granulated bulking agents may be capable of being stored in conventional storage compartments and transferred using conventional transfer apparatus.

In some embodiments, the discrete particles of bulking agent have an average particle size of between about 1 mm and 4 mm (e.g. between about 2 and 3 mm). Such a particle size is similar to that of ammonium nitrate prills commonly used in the explosives industry. Bulking agents having such a particle size can therefore readily be stored and processed using equipment currently used to store and process ammonium nitrate prills.

In some embodiments, the oxidiser component of the explosive (e.g. the aqueous phase in a water in oil explosive emulsion) may comprise a supersaturated solution of an oxidiser. Such a supersaturated solution would not be capable of dissolving any more substances (at constant temperature), therefore potentially further inhibiting migration of the combustible substance from the bulking agent into the oxidiser component.

In some embodiments, the oxidiser component of the explosive may, for example, comprise an oxidiser selected from the group consisting of ammonium nitrate, sodium nitrate, calcium nitrate, ammonium perchlorate and mixtures thereof. In embodiments where the explosive is a water-in-oil emulsion, the oil may be a hydrocarbon.

In some embodiments, the composition comprises between about 50% and about 99% (by weight) of the explosive. Correspondingly, in some embodiments, the composition comprises between about 1% and about 50% (by weight) of the bulking agent. Compositions comprising more than about 50% of the explosive are generally considered to be water resistant, with compositions comprising more than about 60% explosive being preferred. As will be appreciated, increasing the water resistance makes the explosive compositions more suitable for use in wet ground.

In some embodiments, a sensitising agent may be required in order to sensitise (or further sensitise) the explosive composition. In some embodiments, the sensitising agent may be a density reducing agent such as a chemical gassing agent (e.g. a salt of an alkali metal nitrite and an acid, whereby nitrogen gas is generated upon combination of the salt and acid).

In a second aspect, the present invention provides a method for delivering an explosive composition to a borehole (e.g. a borehole in soft and wet ground). The method comprises mixing an explosive comprising an oxidiser component in a water in oil emulsion or a water gel with a bulking agent comprising discrete particles of a combustible and water soluble substance to form an explosive composition; and delivering the explosive composition to the borehole.

In some embodiments the method may further comprise adding a sensitising agent to the explosive composition. The explosive composition may, for example, be sensitised by adding the sensitising agent to the explosive composition (either before or after the explosive and bulking agent have themselves been mixed, as will be discussed further below) before delivery to the borehole.

In some embodiments, the explosive and the discrete particles of bulking agent may be stored before mixing in separate compartments of a conventional mobile processing unit. The discrete particles of bulking agent may, for example, be stored in a compartment of the mobile processing unit typically reserved for ammonium nitrate prills. As will be appreciated, discrete particles (especially prills and granules and those having smooth outer surfaces) would flow in a similar manner to ammonium nitrate prills, and would therefore easily be transferable and hence less likely to contaminate the compartment post use. However, even if a small amount of the bulking agent remained in the compartment, as long as the bulking agent provides no sensitisation to ammonium nitrate prills, then a small amount of residual bulking agent would be unlikely to result in a potentially explosive mixture with any subsequently added ammonium nitrate prills.

In contrast, many prior art bulking agents have little consistency in size distribution and would therefore not be as easy (or reliable) to transfer. Further, as many prior art bulking agents also provide sensitisation to ammonium nitrate prills, if they were stored in compartments reserved for the ammonium nitrate prills, it would always be necessary to thoroughly clean out the compartment after use, otherwise adding ammonium nitrate prills to the compartment might result in a potentially explosive mixture being formed.

The explosive composition used in the method of the second aspect of the present invention may, for example, be the explosive composition of the first aspect of the present invention.

In a third aspect, the present invention provides a method of reducing post-blast fume. The method comprises delivering an explosive composition to a borehole, wherein the explosive composition comprises discrete particles of a water-soluble combustible substance having a negative oxygen balance, wherein the discrete particles are distributed throughout a water-in-oil emulsion or a water gel.

The explosive composition used in the method of the third aspect of the present invention may, for example, be the explosive composition of the first aspect of the present invention.

DESCRIPTION OF EMBODIMENTS

Disclosed herein is an explosive composition suitable for soft and wet ground. The explosive composition comprises an explosive comprising an oxidiser component in a water in oil emulsion or a water gel, and a bulking agent comprising discrete particles of a combustible substance. The combustible substance is water soluble but, in the explosive composition, migration of the combustible substance from the discrete particles to the oxidiser component is inhibited.

Also disclosed herein is a method for delivering an explosive composition to a borehole, for example, a borehole in soft and wet ground. The method comprises mixing an explosive comprising an oxidiser component in a water in oil emulsion or a water gel with a bulking agent comprising discrete particles of a combustible and water soluble substance, to form an explosive composition; and delivering the explosive composition to the borehole. As will be discussed below, the methods of the present invention can also be used in some circumstances where the ground is not soft and wet.

The present invention relates to explosive compositions suitable for use in soft and wet ground. Explosive compositions for soft ground require less energy to make the ground move than is the case for harder ground, and one of the ways to reduce an explosive composition's energy is to incorporate a bulking agent into the composition. Bulking agents reduce the explosive energy by bulking out the composition and, despite being oxidised in the explosion, may or may not be a fuel source for the explosion.

Explosive compositions for wet ground need to have some water resistance, which may be imparted to the composition via a water in oil emulsion or water gel (both of which have inherent water resistance). The explosive composition of the present invention therefore comprises an explosive comprising an oxidiser component in a water in oil emulsion or a water gel.

Any water in oil emulsion or water gel may be used in the explosive composition of the present invention, provided that it is suitable for use (with a bulking agent) in soft and wet ground. It is within the ability of a person skilled in the art to select an appropriate water in oil emulsion or water gel for use in the present invention, based on factors such as the characteristics of the ground to be blasted and the desired blasting outcome.

The oxidiser component of the explosive is the component of the water in oil emulsion or water gel which contains the oxidiser. For example, in the case of a water in oil emulsion, the oxidiser component is the discontinuous aqueous phase. The oxidiser for use in the present invention may be selected from any known oxidisers which are compatible with the intended use of the explosive composition. The oxidiser may, for example, be ammonium nitrate, sodium nitrate, calcium nitrate, ammonium perchlorate or mixtures thereof. Typically, the oxidiser will include or consist essentially of ammonium nitrate.

In some embodiments, the oxidiser component may comprise a supersaturated solution of the oxidiser, which can contribute to inhibiting migration of the combustible substance from the discrete particles of bulking agent to the oxidiser component, simply because the oxidiser component is incapable of (or less likely to be capable of) dissolving any additional substances (at that temperature).

In embodiments where the explosive is a water in oil emulsion, the oil component of the emulsion may be any suitable oil. For example a hydrocarbon fuel oil of the kind typically used in explosive emulsions may be used. Suitable oils include fuel oils such as mineral or diesel oils.

Typically, the oil component of an explosive emulsion is a continuous phase, which can also contribute to inhibiting migration of the combustible substance from the discrete particles of the bulking agent to the oxidiser component or vice versa, simply because the oil component provides a physical, hydrophobic barrier or layer between the two components (at that temperature). In effect, the oil component separates the combustible substance from the oxidiser component.

In embodiments where the explosive is a water in oil emulsion, the emulsion may also include an emulsifier to help form and subsequently stabilise the emulsion. The emulsifier may, for example, be any of the emulsifiers typically used with emulsion blasting explosives. Suitable emulsifiers may, for example, be selected from the group of emulsifiers that result from condensation reactions between PIBSA and amines or alkanolamines. Another suitable emulsifier is sorbitan mono-oleate, or the like. A single emulsifier or a combination of emulsifiers may be used. When present, the emulsifier typically comprises between 0.3 to 3.5% (e.g. 0.5 to 1.5%) by weight of the emulsion.

The explosive composition of the present invention also comprises a bulking agent comprising discrete particles of a combustible water soluble substance.

As used herein, the term "combustible substance" means a substance that would undergo combustion during an explosion. A combustible substance does not necessarily provide fuel during the explosion, but does burn and, in embodiments where the combustible substance has a negative oxygen balance, can act as a sink for the oxygen produced by the oxidiser. As it is a bulking agent, the combustible substance is itself non-explosive, but is capable of being consumed by the explosion.

Providing the bulking agent in the form of discrete particles inhibits migration of the water soluble substance contained in the discrete particles to the oxidiser component, especially over the length of time for which the bulking agent and explosive are likely to be in contact before detonation. As such, despite being formed from water soluble substances which would have been expected to interact with and potentially destabilise the explosive, bulking agents in accordance with the present invention have been found to not destabilise the explosive, even when the explosive and bulking agent are intimately mixed together, as is typically the case. The discovery underlying the present invention therefore enables a new class of substances to be used as bulking agents; namely a class of substances that is water soluble (and otherwise suitable for use as a bulking agent).

Without wishing to be bound by theory, the inventors postulate that migration of the substance from the bulking agent to the oxidiser component is inhibited due to the limited ability of the substance when contained in the discrete particles, to interact with the oxidiser component when mixed. A number of other factors, which are described herein in further detail, can also contribute to inhibiting migration of the substance contained in the discrete particles to the oxidiser component. Indeed, in specific embodiments of the present invention, a number of such factors may contribute to providing optimal explosive compositions for specific applications (e.g. short or long sleep times, relative softness and wetness of the ground to be blasted, etc.).

Providing the bulking agent in the form of discrete particles of a combustible substance can also, in some embodiments, provide a slow burning source of fuel in the explosive composition, which may help to mitigate post blast fumes. As described herein, the particle size of the discrete particles of bulking agent is typically at least an order of magnitude larger than any droplets of the oxidiser in the explosive (the discrete particles of bulking agent typically have a particle size in the millimetres, whilst any droplets of the oxidiser in an ANE (ammonium nitrate emulsion), for example, is micron sized). Without wishing to be bound by theory, the inventors postulate that by providing a slow burning fuel source in the explosive composition, bulking agents in accordance with embodiments of the present invention (and especially those having a negative oxygen balance) may provide an excess of fuel at the point where NOx reaction pathways can become predominant during detonation, and this excess of fuel creates alternative reaction pathways to water and COx, which are more desirable products than NOx fumes. Again, not wishing to be bound by theory, the manufacturing process of an emulsion is such that the ammonium nitrate is dissolved at temperature (15° C. or greater than the crystallisation point). The emulsion is formed when the hot oxidiser and hot fuel (typically about 65° C.) is mixed in some way. The emulsion is then cooled, and when cooled, the product temperature is generally cooled below its crystallisation point and therefore the oxidiser is supersaturated. The reason it does not crystalise and form solid particles is because the Laplace pressure of the droplet has to be overcome for crystallisation to occur. Therefore, in an emulsion the oxidiser droplets are the discrete phase and the fuel phase is the continuous phase.

The combustible substance in the discrete particles of bulking agent is water soluble. However, in the explosive composition, migration of the substance from the discrete particles to the oxidiser component is inhibited. This prevents (or at least significantly slows down) destabilisation of the explosive composition, for example, by causing crystallisation of the oxidiser (or other components) in the oxidiser component. It is within the ability of a person skilled in the art to select, for any given application, an appropriate combustible substance for use as the bulking agent, as well as the form of the discrete particles (e.g. prilled or granulated form). Relatively straightforward tests or field trials can be carried out to ascertain whether a particular substance is suitable for use in a given application of the present invention (e.g. whether it would function as a combustible bulking agent during the explosion), as well as whether migration of the substance from the discrete particles to the oxidiser component is inhibited for commercially realistic periods of time once mixed with the explosive.

For example, the stability of an emulsion or water gel in the presence of discrete particles of bulking agent can be measured using the Rod Rating test (described below), with particles that provide a Rod Rating test result of 6 or higher when mixed with the explosive for an appropriate period of time typically being suitable for use in the present invention.

In the Rod Rating test, blends containing appropriate proportions of an explosive and discrete particles of a bulking agent are prepared and a 10 mm glass rod is dipped into the blend at a 45 degree angle to a depth of approximately 20 mm. This allows for one side of the glass rod to be coated with the blend. The glass rod is then lightly tapped to remove excess bulking agent and/or emulsion/water gel. The glass rod is held toward a light source with the side coated with the emulsion/water gel facing away such that the light can visually pass through the glass rod. The emulsion/water gel is than lightly rubbed along the glass rod three times and the proportion of crystals are measured as follows:
8=no crystals,
7=small amount of crystals,
6=half emulsion/water gel: half crystals,
5=mostly crystals with some emulsion/water gel.
4=All crystals with no emulsion/water gel.

A blend may be continually rated for the proportion of crystal formation over time at known intervals in order to assess its suitability for any given sleep time.

The bulking agent comprises discrete particles of the combustible substance. The discrete particles may have any practical size and shape, provided that migration of the substance into the oxidiser component is inhibited and that the particles function as bulking agents in the explosive composition. In some embodiments, the discrete particles of bulking agents may have smooth outer surfaces, that is, they substantially lack rough surfaces and sharp edges which may promote crystallisation of components in the oxidiser component (e.g. in the aqueous phase of the emulsion). As such, physical interactions between the particles of the bulking agent and the oxidiser component are less likely to promote destabilisation of the explosive composition.

The bulking agent may, for example, be provided in the form of prills or granules. Such prills and granules typically have relatively smooth outer surfaces and are capable of being formed using well-known techniques. Further, prills and granules are two particle types that are commonly used in the explosives industry, and providing the bulking agent in such forms may enable it to be stored and processed without the need for non-conventional equipment. In alternative embodiments, however, the bulking agent may, for example, be provided in the form of fines.

In some embodiments, the bulking agents may be provided in the form of agricultural prills or granules. Agricultural prills, for example, are cheaper to manufacture than other forms of prills (e.g. explosive grade prills), and are typically formed without pores on them (i.e. they have smoother surfaces than explosive grade prills, which may help to further inhibit migration of the combustible substance into the oxidiser component).

The discrete particles of bulking agent may, for example, have a rounded (e.g. substantially spherical) shape, which would impart excellent flowing properties and make the bulking agent easy to pour, pump, auger, etc. Alternatively (or in addition), the particles may, for example, be cylindrical, cube shaped, rectangular block shaped, or irregular in shape, with generally smooth surfaces and rounded edges.

The discrete particles of bulking agent may have any size that enables them to be used in the explosive composition. If the particle size is too small, then it would no longer be categorised as a discrete particle and it would not burn slowly, which may increase the risk of post blast fumes. On the other hand, if the particle size is too large, then it may result in decoupling of the explosive composition and undesirable explosive properties. In some embodiments, the discrete particles may have an average particle size (e.g. diameter) of up to about 1 mm, 2 mm, 3 mm or 4 mm. For example, the discrete particles may have an average particle size of between about 1 and 4 mm, 2 and 4 mm, 3 and 4 mm, 2 and 3 mm or 3 and 4 mm. Discrete particles of bulking agent having an average particle size of between about 2 and 3 mm in diameter will be a similar size to ammonium nitrate prills (e.g. as used to produce ANFO). Particles of bulking agent having this size would therefore be compatible with the loading equipment etc. currently used to transfer ammonium nitrate prills, and such a bulking agent would not require new equipment or new equipment configurations for it to be used in the industry.

The discrete particles of bulking agent may be solid or may contain voids therein. Particles having a compact structure devoid of any significant cavities would have a relatively high density, and would therefore be unlikely to sensitise the explosive composition. However, particles containing significant cavities would have a relatively lower density, and would therefore be more likely to sensitise the explosive composition. In some embodiments, it may be desirable to provide a bulking agent that, when mixed with the explosive, would not sensitise the explosive composition so as to permit an explosion. This operates as a safety feature to prevent accidental triggering of an uncontrolled explosion. Whilst, in such embodiments, the explosive composition would need to be sensitised separately (e.g. at the time it is pumped into the shot holes by gassing the emulsion to reduce its density, as will be described below), this additional step is seen as worthwhile in the interests of safety.

The density of the discrete particles of bulking agents will depend on factors such as the nature of the combustible substance and the form in which it is provided (e.g. the density of granulated and prilled urea is 0.73 to 0.78 g/cc and the density of granulated and prilled ammonium sulphate is 0.8 to 0.9 g/cc). In some embodiments, discrete particles of bulking agent may have a density of between about 0.7 to 1.4 g/cc, for example, between about 0.8 to 1.3 g/cc, between about 0.9 to 1.2 g/cc, between about 1.0 to 1.4 g/cc or between about 0.7 to 1.0 g/cc. The discrete particles of bulking agent may, for example, have an average density of about 0.7. 0.8. 0.9. 1.0, 1.1, 1.2, 1.3 or 1.4 g/cc.

The bulking agent in the explosive composition of the present invention comprises discrete particles of a water soluble combustible substance. A combustible substance will be suitable for use in the present invention if it is (a) water soluble (e.g. has a water solubility of greater than about 1 g/100 mL, 10 g/100 mL, 20 g/100 mL or 40 g/100 mL), (b) will act as a bulking agent in the explosive composition and (c) can be formed into discrete particles. It is within the ability of a person skilled in the art using routine tests to determine whether any given substance is suitable for use as a bulking agent in the present invention.

As it is a bulking agent, the combustible substance must itself be non-explosive, but capable of being consumed by the explosion. Typically, the combustible substance will be a substance having a negative oxygen balance. Such substances reduce the explosive energy of the composition by bulking out the composition, but also provide an oxygen sink, which can help to inhibit the formation of NOx. For example, discrete particles of some of the combustible substances discussed below (e.g. urea) are a slow burning source of fuel and, when there are possible reaction pathways for NOx formation during the explosion, then there is an excess of C and H, which drive the reaction pathways to other species such as COx and water.

Whilst combustible substances having a positive oxygen balance can potentially be used in the present invention, such an explosive composition would be more likely to be under fuelled and hence more likely to result in NOx formation and post blast fumes. Again, relatively straightforward trials could be carried out using such combustible substances to ascertain whether post blast fumes are formed and, if so, whether the amount of the post blast fumes exceeds site requirements.

The combustible substance used to form the discrete particles in the bulking agent may, for example, be an agricultural substance such as a fertiliser. As would be appreciated, such substances are relatively cheap, are generally available and are often provided in a prilled or granulated form which is especially suitable for use in the present invention. It has also been found that some of these substances can help mitigate (or even prevent) the formation of post-blast fumes.

The combustible substance used to form the discrete particles in the bulking agent may, for example, be urea, ammonium sulphate, diammonium phosphate or mixtures thereof. Other combustible substances that might be used, but which have positive oxygen balances, include monoammonium phosphate, calcium ammonium nitrate, zinc sulphate or mixtures thereof.

In specific embodiments of the present invention, the explosive composition comprises a water in oil emulsion and a bulking agent in the form of prills or granules of a fertiliser such as urea or ammonium sulphate. Such explosive compositions have been found to have an appropriate water resistance and explosive energy for use in soft and wet ground, and also produce very little or no post blast fumes during blasting.

Adjusting the proportion of explosive to blasting agent in the explosive composition will affect the strength and water resistance of the explosive composition. For example, the proportion of bulking agent can be selected such that it reduces the theoretical energy of the explosive composition by between about 20 and 30% when compared to a composition containing ammonium nitrate prills or ANFO instead of the bulking agent. As will be appreciated, such a decrease in the theoretical energy makes such explosive compositions more suitable for use in soft ground.

The proportions of the explosive and the bulking agent in the explosive composition are selected based on the conditions at the blast site. As noted above, increasing the proportion of the explosive relative to the bulking agent will increase the explosive energy and water resistance of the composition, but may also result in the composition having a positive oxygen balance (which may result in post blast fumes). Generally, it is desirable that the composition comprises the explosive and the bulking agent in a proportion whereby the composition has an overall negative oxygen balance. It is within the ability of a person skilled in the art to consider relevant factors (and possibly conduct some field trials) to determine the appropriate proportions of explosive and bulking agent in the explosive composition of the present invention for use in a specific location.

In some embodiments, the composition comprises between about 50% and about 99% (by weight) of the explosive. Generally an explosive composition has good water resistance if it contains 60% or more of the water gel or emulsion explosive. As such, in some embodiments, the composition comprises above about 60% (by weight) of the explosive, for example, about 65%, 70%, 75%, 80%, 85%, 90% or 95% (by weight) of the explosive (or any ranges therebetween).

Correspondingly, the explosive composition may comprise between about 1% and about 50% (by weight) of the bulking agent. For example, the composition may comprise about 5%, 10%, 15%, 20%, 25%, 30%, 35%, 40%, 45% or 50% (by weight) of the bulking agent (or any ranges therebetween).

As discussed in further detail below, whilst the explosive and the bulking agent may be provided in a pre-mixed form, it is anticipated that they will typically be stored separately, and combined only when they are being transferred into the blast hole (with other agents, for example sensitising agents as discussed below, being added at about the same time). Typically, the discrete particles of combustible substance are substantially uniformly distributed throughout the water-in-oil emulsion or water gel such that the explosive composition will have consistent properties throughout. In some embodiments, however, advantages may be gained by providing an explosive composition in which the discrete particles of combustible substance are not substantially uniformly distributed throughout the water-in-oil emulsion or water gel. For example, a situation may exist where there may be 25 m holes with a harder rock layer at midway with 5 m of water. The explosive composition of the present invention can be used to a certain depth for the wet weak material and then the composition is changed to a straight emulsion gas sensitised for the harder layer, returning to the composition of the invention for the weaker material above the harder rock layer. Although the particles are homogeneous when loaded, over the whole explosive column, it is not. Another example would be to load the invention on to the walls of the blast hole and then fill the middle of the explosive column with something else, such as ANFO, heavy or slurry. The general advantages of the invention are greater flexibility and to allow higher energy products where the ground geology presents challenges that may not be met using a low energy product.

In embodiments where the bulking agent provides little or no sensitisation to the explosive composition, the composition may further comprise a sensitising agent. Any sensitising agent that is compatible with the other components of the explosive composition and which will not deleteriously affect its explosive properties may be used. Suitable sensitising agents may be selected by a person skilled in the art based on the disclosure herein and factors such as the other components of the explosive composition, the stage at which the sensitising agent is to be added and the desired outcome of the explosion.

The sensitising agent may, for example, be a density reducing agent (especially when the bulking agent is provided in the form of solid prills or granules). In some embodiments, the density reducing agent may be a chemical gassing agent, for example, a salt of an alkali metal nitrite (e.g. sodium nitrite or potassium nitrite) and an acid, whereby nitrogen gas is generated upon combination of the nitrite ion, ammonium ions (from the emulsion or water gel) and acid. In alternative embodiments, the density reducing agent may be glass or plastic microballoons, or occluded air.

The sensitising agent may be added at any time. For example, the sensitising agent may be added to the explosive or the bulking agent, with that mixture subsequently being added to the other of the explosive and bulking agent. Alternatively, the sensitising agent may be added to the mixture of the explosive and bulking agent. However, as the sensitised composition is more explosive, the sensitising agent would typically be added to the explosive composition (or a component of the explosive composition) at the time the composition is being injected into a blast hole (or shortly beforehand). In embodiments where the sensitising agent is an alkali metal nitrite and an acid, when mixed together these compounds produce nitrogen gas, thereby reducing the density of the explosive composition. Ideally, the density of the composition is reduced to less than 1.15 g/cm$^3$, for example, between 0.80 g/cm$^3$ and 1.15 g/cm$^3$, by selecting a suitable quantity of sensitising agent to mix with the composition.

In specific embodiments, an acid (e.g. acetic acid) is added to an ammonium nitrate emulsion (e.g. via a static mixer), and a 20 to 30% solution of sodium nitrite is then added to the acidified ammonium nitrate based emulsion. The nitrite ions are protonated and then react with the ammonium ions to generate nitrogen gas. Generation of the gas is normally completed within 20 to 60 minutes. The amount of the sodium nitrite solution used determines the final density of the explosive composition. The discrete particles of bulking agent are then added, and the resultant mixture then pumped (e.g. using an auger) into the blast hole.

Other substances may also be added the explosive composition, either during its storage (e.g. as separate components) or whilst it is being transferred to the bore hole. For example, enhanced or varied properties of explosive compositions in accordance with the present invention may be obtainable by incorporating ANFO, microballoons or a lubricant (e.g. water) into the composition.

For example, whilst the present invention is directed to explosive compositions suitable for soft and wet ground and hence having relatively lower amount of explosive power, in some embodiments it may be desirable to include ammonium nitrate prills in the explosive composition. Ammonium nitrate prills are not a bulking agent and will increase the explosive power, but their inclusion in the explosive composition of the present invention (i.e. in addition to the explosives and bulking agents disclosed herein) may impart desirable properties to the resultant explosive composition. Including ammonium nitrate prills may, for example, provide a little more explosive energy but whilst reducing NOx formation. The addition of ammonium nitrate or ammonium nitrate fuel oil may be desirable where the geology of the ground has slightly harder rock or if a result with more heave is required, for example.

In use, an explosive composition in accordance with the present invention may be delivered to a borehole, such as in soft and wet ground, using any suitable technique, taking all relevant factors (especially safety) into account. The explosive composition (or its components) may be transferred using any conventional techniques, such as pumping or augering, with additional components being added where necessary.

Typically, the explosive and blasting agent will be stored separately, and the explosive composition delivered to a borehole by first mixing an explosive comprising an oxidiser component in a water in oil emulsion or a water gel with a bulking agent comprising discrete particles of a combustible substance, to form an explosive composition, and then delivering the explosive composition to the borehole.

As discussed above, it may be necessary to sensitise the explosive composition (e.g. using a sensitising agent) either immediately before or during its transfer to the borehole. In order to ensure adequate mixing of the sensitising agent into the explosive composition, the sensitising agent would typically be added before the explosive composition was delivered into the borehole.

In embodiments where the explosive and the discrete particles of bulking agent are stored separately before mixing, they may be stored in separate compartments of a mobile processing unit (MPU) of the type routinely used in the explosives industry. As noted above, in some embodiments, the discrete particles of the bulking agent can have a similar size and shape to that of ammonium nitrate prills, and such discrete particles of bulking agent can therefore be stored in the compartment of the mobile processing unit typically reserved for ammonium nitrate prills.

As would be appreciated, providing a new explosive composition with properties making it suitable for use in such ground as soft and wet ground, but which can utilise existing equipment, would be of enormous benefit to the industry. Further, as the discrete particles of bulking agent typically have good flowing properties and a lack of fines, the compartment of the MPU which had been used to hold the bulking agent would be easy to clean after use, thereby substantially alleviating potential contamination issues. Furthermore, as the discrete particles of bulking agent are typically non-sensitising of ammonium nitrate prill, in the event that some of these particles were mixed with prills of ammonium nitrate, the likelihood of them providing a source of ignition, fuel for the ammonium nitrate prill or enough sensitisation to form a potentially explosive mixture with the ammonium nitrate prill is extremely low. Therefore the MPU trucks can be used for either arrangement and easily re-purposed, to carry either set of blasting components.

In a specific embodiment, the explosive compositions of the present invention can be delivered to a site where blasting is to take place using a conventional MPU truck, which is carrying the components in the sections normally used to hold the components of traditional AN emulsion blasting agents. As will be appreciated, a MPU typically has three sections, with the first and smallest section usually containing fuel oil, which traditionally comprises about 6% of the ANFO component. The second section is normally used for storage of the ammonium nitrate prills for dry addition, and the third section for storage of the ammonium nitrate based emulsion (or water gel).

The explosive composition may be delivered from an auger of the MPU, which may facilitate mixing of the discrete particles of the bulking agent with the explosive, with the density reducing agent (when necessary) ideally being added to the explosive composition before the explosive composition exits from the auger into the blast holes. If the density reducing agent is an alkaline metal nitrite salt, for example, then a salt solution can be administered through an inlet port into the emulsion stream before the explosive composition is delivered out the auger and into a blast hole.

As discussed herein, aspects and embodiments of the present invention can provide a reduction in post-blast fumes. In this regard, the present invention may provide a method of reducing post-blast fume, comprising delivering an explosive composition to a borehole, wherein the explosive composition comprises discrete particles of a water-soluble combustible substance having a negative oxygen balance, wherein the discrete particles are distributed throughout a water-in-oil emulsion or a water gel. The explosive composition used in this method may, for example, be the explosive composition of the first aspect of the present invention.

In some embodiments, the discrete particles are uniformly distributed throughout the water-in-oil emulsion or water gel. In some embodiments, the discrete particles are separated from an oxidizer phase of the water-in-oil emulsion by an oil phase.

In some embodiments, the method further comprises adding a sensitising agent to the explosive composition. For example, the explosive composition may be sensitised by adding the sensitising agent to the explosive before it is mixed with the bulking agent and delivered to the borehole.

In some embodiments, the explosive and the discrete particles of bulking agent may be stored before mixing in separate compartments of a mobile processing unit. For example, the discrete particles of bulking agent may be stored in a compartment of the mobile processing unit typically reserved for ammonium nitrate prills.

In some embodiments, the explosive composition may be delivered to the borehole by augering.

Explosive compositions according to the invention, and their method of delivery into blast holes are particularly of benefit when blasting soft, wet ground, such as natural surfaces. The explosive compositions are, however, also useful for applications where blasting effects on adjacent shots are to be minimised. For example, mines experience overbreak from a variety of factors such as block heave and load release from blast damage derived from blasting of the previous adjacent shot. This overbreak can make the ground less competent and allow some explosive composition to runaway, potentially resulting in over charging of the holes. The consequence of this is a greater risk of wall instability, rockslide, ore dilution and non-ideal blasting performance such as greater risk of fume and fly rock. One way of reducing the risk of this is to presplit the last row of the shot that borders to next shot with an explosive composition that has reduced energy. This creates an artificial crack which is better controlled and reduces the risks described. Due to the requirements for a reduced energy explosive, the explosive composition of the present invention would be well suited for this application. The invention is also of benefit when fume mitigation is of importance, as blasts in which the bulking agents have a negative oxygen balance will typically produce a minimum amount of fumes, especially of noxious NOx fumes (which may often be caused when the composition is sensitised using nitrogen gas).

Examples of explosive compositions in accordance with embodiments of the present invention are described below.

EXAMPLES

Example 1—Stability and Water Resistance

Granulated ammonium sulphate and granulated urea (20%, by weight of the explosive composition) were mixed with a standard water in oil ammonium nitrate emulsion (80%, by weight of the explosive composition, see formulation below in Table 1) and chemically gassed using a mixture of sodium nitrite solution (25 wt %) and acetic acid solution (50 wt %) in order to prepare explosive compositions in accordance with embodiments of the present invention.

TABLE 1

| Standard AN Emulsion Formulation | |
|---|---|
| Oxidiser Component | 94% |
| Ammonium Nitrate | 75% |
| Water | 25% |
| Fuel Component | 6% |
| Emulsifier | 15% |
| Mineral Oil/Fuel Oil | 85% |

The stability and water resistance of these explosive compositions were measured and compared with the stability and water resistance of the same water in oil emulsion, but which had been mixed with ANFO in a ratio of 60 and 40 wt %, respectively, and chemically gassed using a mixture of sodium nitrite solution (25 wt %) and acetic acid solution (50 wt %). The results are shown below:

TABLE 2

| Water resistance and stability results after 14 days for Example 1 | | | |
|---|---|---|---|
| | ANE (60 wt %) + ANFO (40 wt %), chemically sensitised | ANE (80 wt %) + Granulated Urea (20 wt %), chemically sensitised | ANE (80 wt %) + Granulated Ammonium Sulphate (20 wt %), chemically sensitised |
| Swell (mm) | 11 | 8 | 8 |
| Penetration (mm) | 4 | 1 | 1 |
| Stability (Rod Rating) | 7 | 7.5 | 7 |

The static water resistance of each explosive composition was measured as follows. 300 g of each blend was put into a 500 mL plastic jar, with an outline of the top of the composition being marked on the outside of the jar using a pen. 150 mL of water is then added to the top of the explosive composition. Over time, water was absorbed into the explosive composition which leads to the blend swelling.

Water also penetrates into the blend and the blend changes to an opaque colour. The height (in centimetres) in which the blend has swelled past the line is the swell. The depth in centimetres which the water has penetrated into the blend is the penetration. The static water resistance was monitored at regular intervals over a 2 week period.

The stability of each explosive composition was measured by monitoring the level of crystallisation in the emulsion as a function of time. This was achieved by performing the Rod Rating test described above.

Improvements were observed for the water resistance of the two explosive compositions in accordance with embodiments of the present invention compared to the standard, indicating that explosive compositions in accordance with the present invention are at least as water resistant and stable as conventional water resistant explosives. The compositions in accordance with the present invention are also at least as stable as the standard composition.

No evidence of shrinkage of the granules of urea and ammonium sulphate in the explosive compositions in accordance with the present invention was observed during the Rod Rating tests over the 2 week period.

Example 2—Velocity of Detonation

VOD testing was performed for a standard ammonium nitrate emulsion formulation (100 wt %), and was compared with a composition in accordance with an embodiment of the present invention (Example 2A) containing the same emulsion formulation (80 wt %) mixed with granulated urea (20 wt %). Both of the mixtures were chemically sensitised by adding 0.03 wt % sodium nitrite solution and 0.03 wt % acetic acid solution (50 wt %). The mixtures were loaded into either 100 mm or 150 mm diameter pipe and the formulations and their respective velocity of detonation are outlined below:

TABLE 3

VOD results for Example 2

|  | Standard | Example 2A |
|---|---|---|
| ANE (wt %) | 100 | 80 |
| Urea Prill (wt %) | 0 | 20 |
| Energy (MJ/kg) | 2.7 | 2 |
| VOD (63 mm diameter pipe) (m/s) | 4700 | 4000 |
| VOD (100 mm diameter pipe) (m/s) | 4700 | 4600 |
| VOD (150 mm diameter pipe) (m/s) | 5100 | 5000 |

As can be seen, the explosive composition in accordance with an embodiment of the present invention has a significantly lower energy and comparable, but slightly lower VODs than a standard ANE explosive composition when the charge diameter was 100 or 150. As can be seen, this difference became greater at smaller diameter due to the difference in energy between the two products (and as both products approach the critical diameter). As would be appreciated, these data can be correlated with the compositions of the present invention having a lower heave and energy than standard ANE explosive compositions.

Example 3—Velocity of Detonation (VOD) Increased Blends

VOD testing was performed for a standard ammonium nitrate emulsion formulation (100 wt %), and was compared with embodiments in accordance with the present invention.

A batch of Ammonium Nitrate Emulsion (ANE) was prepared for use in preparing emulsion-prilled urea blends (see Mixes 1-4 below) in accordance with embodiments of the present invention. The emulsion was prepared by adding a mixture of ammonium nitrate (80 wt %) and water (20 wt %) to a 2000 mL stainless steel jug. The salt and water were heated to 80° C. to enable the ammonium nitrate to become dissolved. In a separate 1000 mL stainless steel beaker, PIBSA based emulsifier (15 wt %), mineral oil/diesel (85 wt %) were added. This mixture was heated to 70° C. where it became a mono-dispersed liquid. The fuel mixture was stirred using a 64 mm diameter jiffy blade fitted to an overhead mixer. The oxidiser solution was added to the fuel mixture while continuing to stir with the overhead mixer. The resulting emulsion had an oxidiser to fuel ratio of 94:6, respectively. After all the oxidiser had been added, a low viscosity emulsion had formed. Further refinement was applied resulting in an emulsion of 32,000 cP when using a Brookfield viscometer at 20 rpm and using a spindle 7. The product was cooled before blending with urea.

Four mixes in accordance with embodiments of the present invention were made. In Mix #1, the base emulsion was mixed with prilled urea in a weight ratio of 60:40 until the prill was uniformly dispersed in the emulsion. In Mix #2, the base emulsion was mixed with prilled urea in a weight ratio of 65:35 until the prill was uniformly dispersed in the emulsion. In Mix #3, the base emulsion was mixed with prilled urea in a weight ratio of 70:30 until the prill was uniformly dispersed in the emulsion. In Mix #4, the base emulsion was mixed with prilled urea in a weight ratio of 80:20 until the prill was uniformly dispersed in the emulsion.

The mixes were acidified with acetic acid and a nitrite solution added until the mixture had achieved a nominal density of 1.10 g/cc (~0.08 wt % sodium nitrite of the total blend). The product was loaded into PVC pipes with diameters 100 mm, 125 mm and 150 mm. The product was initiated using different boosters to test sensitivity. The Velocity of Detonation was measured using the point to point method.

The results are shown in Table 4 and indicate the product detonates at full order with a one pound booster when emulsion, urea prill, and chemical gassing are used in the quantities disclosed. For all mixes, ungassed blend loaded into a 150 mm diameter pipe failed to initiate with a one pound booster, indicating that the urea does not provide sensitisation to the ANE. Mixes 1 and 2 detonated ("det") with a 50 gram booster, but not with a 20 gram booster. Mixes 3 and 4 detonated with a 20 gram booster, but not with a 10 gram booster.

TABLE 4

VOD results for Example 3

| Mix # | Diameter | Density (g/cc) | Booster | VOD (m/s) |
|---|---|---|---|---|
| 1 (40% UREA) | 150 mm | 1.30 No Gas | 1 lb | Fail |
| 1 (40% UREA) | 150 mm | 1.14 | 1 lb | 3800 |
| 1 (40% UREA) | 150 mm | 1.05 | 1 lb | 3800 |
| 1 (40% UREA) | 150 mm | 1.04 | 1 lb | 3800 |
| 1 (40% UREA) | 125 mm | 1.03 | 1 lb | 3700 |
| 1 (40% UREA) | 100 mm | 1.04 | 1 lb | 3400 |
| 1 (40% UREA) | 150 mm |  | 20 g | Fail |
| 1 (40% UREA) | 150 mm |  | 50 g | Det |
| 2 (35% UREA) | 150 mm | 1.32 No Gas | 1 lb | Fail |
| 2 (35% UREA) | 150 mm | 1.13 | 1 lb | 4100 |
| 2 (35% UREA) | 150 mm | 1.03 | 1 lb | 4000 |
| 2 (35% UREA) | 150 mm | 1.03 | 1 lb | 4100 |

TABLE 4-continued

VOD results for Example 3

| Mix # | Diameter | Density (g/cc) | Booster | VOD (m/s) |
|---|---|---|---|---|
| 2 (35% UREA) | 125 mm | 1.05 | 1 lb | 4000 |
| 2 (35% UREA) | 100 mm | 1.04 | 1 lb | 3600 |
| 2 (35% UREA) | 150 mm | | 20 g | Fail |
| 2 (35% UREA) | 150 mm | | 50 g | Det |
| 3 (30% UREA) | 150 mm | 1.34 No Gas | 1 lb | Fail |
| 3 (30% UREA) | 150 mm | 1.15 | 1 lb | 4300 |
| 3 (30% UREA) | 150 mm | 1.05 | 1 lb | 4200 |
| 3 (30% UREA) | 150 mm | 1.04 | 1 lb | 4400 |
| 3 (30% UREA) | 125 mm | 1.08 | 1 lb | 4200 |
| 3 (30% UREA) | 100 mm | 1.06 | 1 lb | 3700 |
| 3 (30% UREA) | 150 mm | | 20 g | Det |
| 3 (30% UREA) | 150 mm | | 10 g | Fail |
| 4 (20% UREA) | 150 mm | 1.37 No Gas | 1 lb | Fail |
| 4 (20% UREA) | 150 mm | 1.17 | 1 lb | 4600 |
| 4 (20% UREA) | 150 mm | 1.04 | 1 lb | 4300 |
| 4 (20% UREA) | 125 mm | 1.06 | 1 lb | 4300 |
| 4 (20% UREA) | 100 mm | 1.09 | 1 lb | 4000 |
| 4 (20% UREA) | 150 mm | | 20 g | Det |
| 4 (20% UREA) | 150 mm | | 10 g | Fail |

Example 4—Post-Blast Fume Mitigation

A series of trials using blends in accordance with embodiments of the present invention including TITAN 9000 (80 wt %), a commercially available ammonium nitrate emulsion, and granulated urea (20 wt %) were carried out at a mine with soft overburden.

The granulated urea was loaded into the bin of the MPU usually reserved for AN prill (i.e. before mixing with the TITAN 9000 ANE and sensitising agent), with the truck being calibrated to account for the slight difference in density between the urea prill and the AN prill. The granulated urea was uniformly dispersed throughout the emulsion immediately before delivery to the borehole. The explosive compositions were chemically sensitised using a sodium nitrite solution and acetic acid solution (50 wt %) to an open cup density of between 0.9-1.15 g/cc.

A first trial involved loading 12 tonnes (approx.) of this product into a number of wet and dry blast holes, recording the following parameters; visual inspection for product quality, gassing rates, VoD, and fume generation for this product, and comparing these parameters with those obtained using the standard explosive compositions used at the mine. The product gassed as expected with VoDs in the range of 4,300 and 4,800 m/s, which is slightly lower than that of the standard explosive (4500-5000 m/s). No post-blast fume was observed from the section of the shot that was loaded with the urea-blended ANE.

A second trial involved loading 60 tonnes (approx.) of this product into blast holes having a depth of 5-13 meters. The VOD monitored blast holes were mainly wet holes. The product gassed as expected with VOD in the range of 3,900 and 4,600 m/s. No post-blast fume was observed.

A third trial involved loading 54 tonnes (approx.) of this product into 145 blast holes having a depth of 16-19 meters. The VOD monitored blast holes were all dry holes. The product gassed as expected with VOD in the range of 3,600 and 5,100 m/s. No post-blast fume was observed.

A fourth trial involved loading 54 tonnes (approx.) of this product into 118 blast holes having a depth of 16-27 meters, with 22 of the holes having a depth of 25-27 meters. All VOD measured blast holes had a depth of 25-27 meters and were dry holes. The product gassed as expected with VOD in the range of 4,600 and 5,100 m/s. No post-blast fume was observed.

A fifth trial involved loading 70 tonnes (approx.) of this product into 145 blast holes. The VOD measured blast holes had a depth of 13-15 meters and were a mix of dry and wet holes. Seven of the blast holes, not VOD measured holes, were loaded with product gassed to a density of 0.85 g/cc. Those holes were monitored for slumping and no slumping was observed. VOD was in the range of 5,100 and 5,200 m/s. No post-blast fume was observed.

These trials clearly demonstrate that compositions in accordance with the present invention can be used in boreholes that are not necessarily in soft and wet ground, provided that maximum explosive power is not required (e.g. in pre-splitting situations, such as those discussed above).

Whilst there have been described herein particular embodiments of the present invention, the described embodiments are to be considered in all respects as illustrative only and it is to be appreciated that modifications can be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that any prior art publication referred to herein does not constitute an admission that the publication forms part of the common general knowledge in the art.

The invention claimed is:

1. An explosive composition for soft and wet ground comprising:
    an explosive comprising an oxidizer component in a water in oil emulsion or a water gel; and
    a bulking agent comprising solid discrete particles of a combustible substance, wherein the bulking agent is not ammonium nitrate prill and wherein the proportion of bulking agent is sufficient to reduce the theoretical energy of the explosive composition by between about 20 and 30% when compared to a composition containing ammonium nitrate prills or ANFO instead of the bulking agent,
    whereby the combustible substance is water soluble, but is resistant to being dissolved in the composition so that migration of the combustible substance from the discrete particles to the oxidizer component is inhibited, and wherein the discrete particles of the solid combustible substance are shaped to have smooth outer surfaces, such that the smooth outer surfaces resists the dissolution thereof into the oxidizer component, and the water-soluble combustible substance remains in the composition in the form of solid, discrete particles,
    wherein an open cup density of the explosive composition is reduced to less than 1.15 g/cm$^3$ to reduce the power of the explosive composition and to enable the composition to be usable in soft and wet ground.

2. The explosive composition of claim 1, wherein the combustible substance has a negative oxygen balance.

3. The explosive composition of claim 1, wherein the combustible substance is an agricultural substance.

4. The explosive composition of claim 1, wherein the combustible substance is a fertilizer.

5. The explosive composition of claim 1, wherein the combustible substance is selected from the group consisting of urea, ammonium sulphate, diammonium phosphate, monoammonium phosphate, calcium ammonium nitrate, zinc sulphate, ammonium sulphate nitrate and mixtures thereof.

6. The explosive composition of claim 1, wherein the bulking agent is provided in the form of prills or granules mixed with the explosive in a mobile processing unit prior to delivery to the soft and wet ground.

7. The explosive composition of claim 1, wherein the bulking agent is provided in the form of agricultural prills or granules mixed with the explosive in a mobile processing unit prior to delivery to the soft and wet ground.

8. The explosive composition of claim 1, wherein the solid discrete particles of bulking agent have a rounded shape.

9. The explosive composition of claim 1, wherein the solid discrete particles of bulking agent have an average particle size of between about 1 mm and about 4 mm.

10. The explosive composition of claim 1, wherein the solid discrete particles of bulking agent have a density of between about 0.7 and about 1.4 g/cc.

11. The explosive composition of claim 1, wherein the oxidizer component comprises a supersaturated solution of an oxidizer.

12. The explosive composition of claim 1, wherein the oxidizer component comprises an oxidizer which is selected from the group consisting of ammonium nitrate, sodium nitrate, calcium nitrate, ammonium perchlorate and mixtures thereof.

13. The explosive composition of claim 1 wherein the composition comprises between about 50% and about 99% (by weight) of the explosive.

14. The explosive composition of claim 1 wherein the composition comprises between about 1% and about 50% (by weight) of the bulking agent.

15. The explosive composition of claim 1, further comprising a sensitizing agent.

16. The explosive composition of claim 15, wherein the sensitizing agent is a density reducing agent and is provided in a sufficient amount in conjunction with the bulking agent to reduce the open cup density of the explosive composition to less than 1.15 g/cm$^3$.

17. The explosive composition of claim 16, wherein the density reducing agent is a chemical gassing agent.

18. The explosive composition of claim 17, wherein the chemical gassing agent comprises a salt of an alkali metal nitrite and an acid, whereby nitrogen gas is generated upon combination of the salt and acid.

19. The explosive composition of claim 1, wherein the combustible substance is solid prill urea.

20. The oxidizer component of claim 12, wherein the oxidizer component is in an aqueous phase of the water in oil emulsion.

21. The explosive composition of claim 1, wherein the discrete particles of bulking agent have a density of about 0.73 to about 0.78 g/cc and are included in a sufficient amount to reduce the open cup density of the explosive composition to less than 1.15 g/cm$^3$.

22. The explosive composition of claim 14, comprising at least about 20% (by weight) of the bulking agent.

23. An explosive composition for soft and wet ground comprising:
    an explosive comprising an oxidizer component in a water in oil emulsion or a water gel;
    from about 20% to about 50% (by weight) of a bulking agent comprising solid and smooth discrete particles of urea;
    a sensitizing agent distinct from the bulking agent; and
    wherein the explosive composition has the following features making it suitable for soft and wet ground:
    does not include ammonium nitrate prill,
    an open cup density of less than 1.15 g/cm$^3$, and
    a negative oxygen balance.

24. The explosive composition of claim 23, wherein the combustible substance is selected from the group consisting of urea, ammonium sulphate, diammonium phosphate, monoammonium phosphate, calcium ammonium nitrate, zinc sulphate, ammonium sulphate nitrate and mixtures thereof.

25. The explosive composition of claim 23, wherein the bulking agent is provided in the form of agricultural prills or granules of urea mixed with the explosive in a mobile processing unit prior to delivery to the soft and wet ground.

26. The explosive composition of claim 23, wherein the solid discrete particles of bulking agent have a rounded shape.

27. The explosive composition of claim 23, wherein the solid discrete particles of bulking agent have an average particle size of between about 1 mm and about 4 mm.

28. The explosive composition of claim 23, wherein the oxidizer component comprises a supersaturated solution of an oxidizer.

29. The explosive composition of claim 23, wherein the oxidizer component comprises an oxidizer which is selected from the group consisting of ammonium nitrate, sodium nitrate, calcium nitrate, ammonium perchlorate and mixtures thereof.

30. The explosive composition of claim 23 wherein the composition comprises between about 50% and about 99% (by weight) of the explosive.

31. The explosive composition of claim 23 wherein the composition comprises between about 1% and about 50% (by weight) of the bulking agent.

32. The explosive composition of claim 23, wherein the sensitizing agent is a density reducing agent and is provided in a sufficient amount in conjunction with the bulking agent to reduce the open cup density of the explosive composition to less than 1.15 g/cm$^3$.

33. The explosive composition of claim 32, wherein the density reducing agent is a chemical gassing agent.

34. The explosive composition of claim 33, wherein the chemical gassing agent comprises a salt of an alkali metal nitrite and an acid, whereby nitrogen gas is generated upon combination of the salt and acid.

* * * * *

UNITED STATES PATENT AND TRADEMARK OFFICE
CERTIFICATE OF CORRECTION

PATENT NO. : 10,906,849 B2
APPLICATION NO. : 15/521959
DATED : February 2, 2021
INVENTOR(S) : Paris et al.

Page 1 of 1

It is certified that error appears in the above-identified patent and that said Letters Patent is hereby corrected as shown below:

In the Specification

Column 7, Line 49 reads, ". . . gel is than lightly . . ." which should read, ". . . gel is then lightly . . ."

Column 11, Line 58 reads, ". . . be added the explosive . . ." which should read, ". . . be added to the explosive . . ."

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*